(12) United States Patent
Choi et al.

(10) Patent No.: US 9,581,842 B2
(45) Date of Patent: Feb. 28, 2017

(54) LIQUID CRYSTAL MODULATOR FOR DETECTING A DEFECTIVE SUBSTRATE AND INSPECTION APPARATUS HAVING THE SAME

(71) Applicant: SAMSUNG DISPLAY CO., LTD., Yongin, Gyeonggi-Do (KR)

(72) Inventors: Suk Choi, Seongnam-si (KR); Sung-Mo Gu, Daegu (KR); Youngjin Noh, Namyangju-si (KR); Youngwon Kim, Yongin-si (KR); Changhyun Ryu, Cheonan-si (KR); Chi Youn Chung, Seoul (KR); Seunghee Lee, Jeonju-si (KR); Young Eun Choi, Jeonju-si (KR)

(73) Assignees: SAMSUNG DISPLAY CO., LTD., Yongin, Gyeonggi-Do (KR); SAMSUNG ELECTRONICS CO., LTD., Suwon-si, Gyeonggi-do (KR); INDUSTRIAL COOPERATION FOUNDATION CHONBUK NATIONAL UNIVERSITY, Deonju-si, Jeonbuk (KR)

( * ) Notice: Subject to any disclaimer, the term of this patent is extended or adjusted under 35 U.S.C. 154(b) by 129 days.

(21) Appl. No.: 14/247,873

(22) Filed: Apr. 8, 2014

(65) Prior Publication Data
US 2015/0085200 A1 Mar. 26, 2015

(30) Foreign Application Priority Data
Sep. 23, 2013 (KR) .................. 10-2013-0112696

(51) Int. Cl.
*G02F 1/13* (2006.01)
*G01N 21/88* (2006.01)
(Continued)

(52) U.S. Cl.
CPC ....... *G02F 1/1309* (2013.01); *G01N 21/8806* (2013.01); *G01N 2021/8848* (2013.01);
(Continued)

(58) Field of Classification Search
CPC ..................... G01N 21/8806; G02F 1/1309
See application file for complete search history.

(56) References Cited

U.S. PATENT DOCUMENTS 5,825,448 A * 10/1998 Bos .................. G02F 1/133753
349/128
2003/0215129 A1 * 11/2003 Yang ..................... G06T 7/0002
382/149

(Continued)

FOREIGN PATENT DOCUMENTS

JP 2009-047476 3/2009
KR 10-0778148 11/2007
(Continued)

OTHER PUBLICATIONS

English Abstract Publication No. 10-2005-0046263 (for KR 10-0987890).
(Continued)

*Primary Examiner* — James Dudek
(74) *Attorney, Agent, or Firm* — F. Chau & Associates, LLC

(57) ABSTRACT

An inspection apparatus for detecting a defect of a substrate is provided. The inspection apparatus includes a liquid crystal modulator, a light emitting unit, a beam splitter, and a measurement unit. The liquid crystal modulator includes a reflection layer, a liquid crystal layer, an electrode, and a polarizer. The reflection layer reflects a light. The sensor layer includes a hybrid aligned nematic liquid crystal. The electrode is provided on the liquid crystal layer. The polarizer is provided on the electrode.

19 Claims, 12 Drawing Sheets

(51) Int. Cl.
G02F 1/1337 (2006.01)
G01N 21/95 (2006.01)
(52) U.S. Cl.
CPC ............... *G01N 2021/9513* (2013.01); *G01N 2201/067* (2013.01); *G02F 1/1303* (2013.01); *G02F 2001/133773* (2013.01)

(56) References Cited

U.S. PATENT DOCUMENTS

| | | | |
|---|---|---|---|
| 2007/0076133 A1* | 4/2007 | Shimizu | G02F 1/133536 349/5 |
| 2008/0116928 A1 | 5/2008 | Kim et al. | |
| 2010/0060811 A1* | 3/2010 | Yamazaki | G02F 1/134363 349/33 |
| 2010/0066960 A1* | 3/2010 | Smith | G02F 1/1323 349/128 |
| 2010/0177313 A1* | 7/2010 | Jun | G01R 31/308 356/366 |

FOREIGN PATENT DOCUMENTS

| | | |
|---|---|---|
| KR | 10-2009-0025877 | 3/2009 |
| KR | 10-2009-0082737 | 7/2009 |
| KR | 10-2006-0092367 | 8/2009 |
| KR | 10-2010-0095048 | 8/2010 |
| KR | 10-0987890 | 10/2010 |
| KR | 10-1042089 | 6/2011 |
| KR | 1020140144958 | 12/2014 |

OTHER PUBLICATIONS

English Abstract Publication No. 10-2007-0090153 (for KR 10-1042089).

* cited by examiner

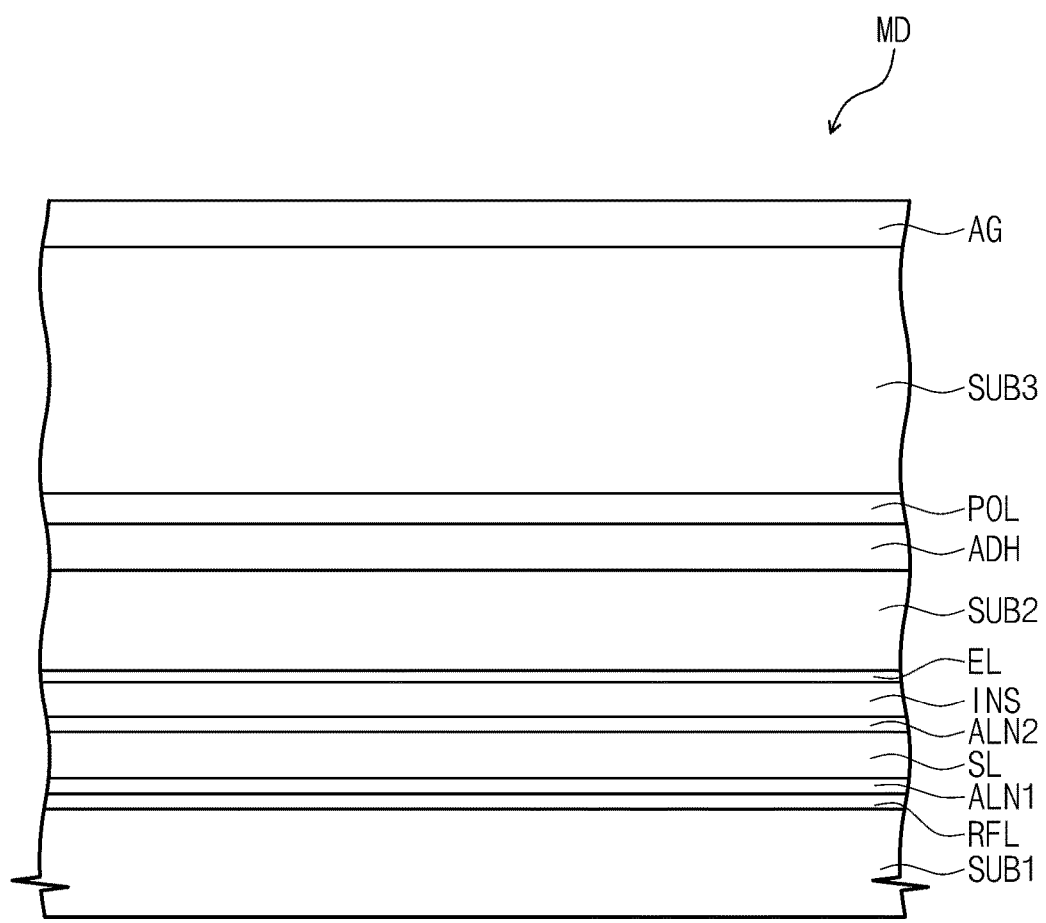

LIQUID CRYSTAL MODULATOR FOR DETECTING A DEFECTIVE SUBSTRATE AND INSPECTION APPARATUS HAVING THE SAME

CROSS-REFERENCE TO RELATED PATENT APPLICATIONS

This application claims priority under 35 U.S.C. §119 to Korean Patent Application No. 10-2013-0112696, filed on Sep. 23, 2013, in the Korean Intellectual Property Office, the disclosure of which is incorporated by reference herein in its entirety.

TECHNICAL FIELD

This disclosure relates to a liquid crystal modulator and, more particularly, to a liquid crystal modulator for detecting a defective substrate and an inspection apparatus having the same.

DISCUSSION OF THE RELATED ART

Display devices such as a liquid crystal display (LCD), an organic light emitting display (OLED), and a plasma discharge panel (PDP) have been developed. These display devices may be able to display high-definition in quality, ultra-thin light weight, and may have wide viewing angle characteristics.

In general, a display device may include pixels for displaying an image. Each pixel may include a pixel electrode and a driving circuit (e.g., a thin film transistor). The driving circuit is electrically connected to the pixel electrode in a one-to-one correspondence manner. Testing may be performed on the pixel electrodes and the driving circuits to detect a defect of a display device to maintain high quality during manufacturing.

SUMMARY OF THE INVENTION

According to an embodiment of the present inventive concept, an inspection apparatus for detecting a defect of a substrate is provided. In an embodiment, the inspection apparatus may include a liquid crystal modulator, a light emitting unit, a beam splitter, and a measurement unit. The light emitting unit may be configured to emit light. The beam splitter may be configured to divide the light emitted from the light emitting unit into a plurality of lights and to provide the plurality of lights to the liquid crystal modulator. The measurement unit may be configured to sense a plurality of lights output from the liquid crystal modulator.

In an embodiment, the liquid crystal modulator may include a reflection layer, a liquid crystal layer, an electrode, and a polarizer. The reflection layer may be configured to reflect the plurality of lights provided from the beam splitter. The liquid crystal layer may be provided on the reflection layer and may include a hybrid aligned nematic liquid crystal. The electrode may be provided on the liquid crystal layer. The polarizer may be provided on the electrode.

In an embodiment, the liquid crystal modulator may further include a first alignment layer provided between the liquid crystal layer and the electrode and a second alignment layer provided between the reflection layer and the liquid crystal layer. One of the first and second alignment layers may be a horizontal alignment layer and the other may be a vertical alignment layer.

In an embodiment, a rubbing axis of the horizontal alignment layer may be titled at an angle of about 45 degrees with respect to a polarizing axis of the polarizer.

In an embodiment, the liquid crystal modulator may be driven in a normally black mode.

In an embodiment, the liquid crystal modulator may further include a quarter wave plate provided between the electrode and the polarizer. In this case, the liquid crystal modulator may be driven in a normally white mode.

In an embodiment, the quarter wave plate may be titled at an angle of about 45 degrees with respect to a polarizing axis of the polarizer and have an optical axis substantially parallel or vertical to a rubbing axis of the horizontal alignment layer.

In an embodiment, a pretilt angle of the vertical alignment layer may be between about 89 degrees and about 90 degrees. A pretilt angle of the horizontal alignment layer may be two degrees or less.

In an embodiment, the hybrid aligned nematic liquid crystal may have positive dielectric anisotropy.

In an embodiment, the liquid crystal layer may delay a phase of one of polarization components of light incident to the liquid crystal layer by a quarter wavelength.

In an embodiment, the liquid crystal modulator may include a polarizer, a liquid crystal layer, and a reflection layer. The polarizer may be configured to receive light and provide polarization component therefrom. The liquid crystal layer may be configured to receive the polarized light from the polarizer, to send a light passing through the liquid crystal layer to a reflection layer, to receive a reflected light from the reflection layer, and to send a light passing through the liquid crystal layer to the polarizer. The reflection layer may be configured to reflect the light output from the liquid crystal layer. The liquid crystal layer may include a hybrid aligned nematic liquid crystal molecules. The hybrid aligned nematic liquid crystal molecules may be arranged depending on an applied voltage to the liquid crystal layer.

In an embodiment, a polarization state of a light passing through the liquid crystal layer may depend on an arranged state of the hybrid aligned nematic liquid crystal molecules.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein:

FIG. 2 is a cross-sectional view of a liquid crystal modulator in FIG. 1;

FIGS. 3A and 3B are perspective views illustrating that an inspection apparatus according to an embodiment of the present inventive concept is driven in a normally black mode, wherein FIG. 3A shows a case when a voltage is not applied to a liquid crystal modulator and FIG. 3B shows a case when a voltage is applied to a liquid crystal modulator;

FIGS. 6A and 6B are perspective views illustrating that an inspection apparatus according to an embodiment of the present inventive concept is driven in a normally white mode, wherein FIG. 6A shows a case when a voltage is not applied to a liquid crystal modulator and FIG. 6B shows a case when a voltage is applied to a liquid crystal modulator;

FIGS. 7A and 7B show voltage-dependent transmittances when a conventional liquid crystal modulator and a liquid crystal modulator according to an embodiment of the present inventive concept are used, respectively, wherein FIG. 7A is a graph of a voltage-dependent transmittance when a twisted nematic (TN) mode liquid crystal is adopted and FIG. 7B is a graph of a voltage-dependent transmittance when a hybrid aligned nematic (HAN) mode liquid crystal according to an embodiment of the present inventive concept is adopted;

FIGS. 8A and 8B show transmittances depending on a pixel configuration when a conventional liquid crystal modulator and a liquid crystal modulator according to an embodiment of the present inventive concept are used, respectively, wherein FIG. 8A is a graph of a transmittance when aTN mode liquid crystal is adopted and FIG. 8B is a graph of a transmittance when a HAN mode liquid crystal according to an embodiment of the present inventive concept is adopted.

DETAILED DESCRIPTION OF THE EMBODIMENTS

Figure 1:
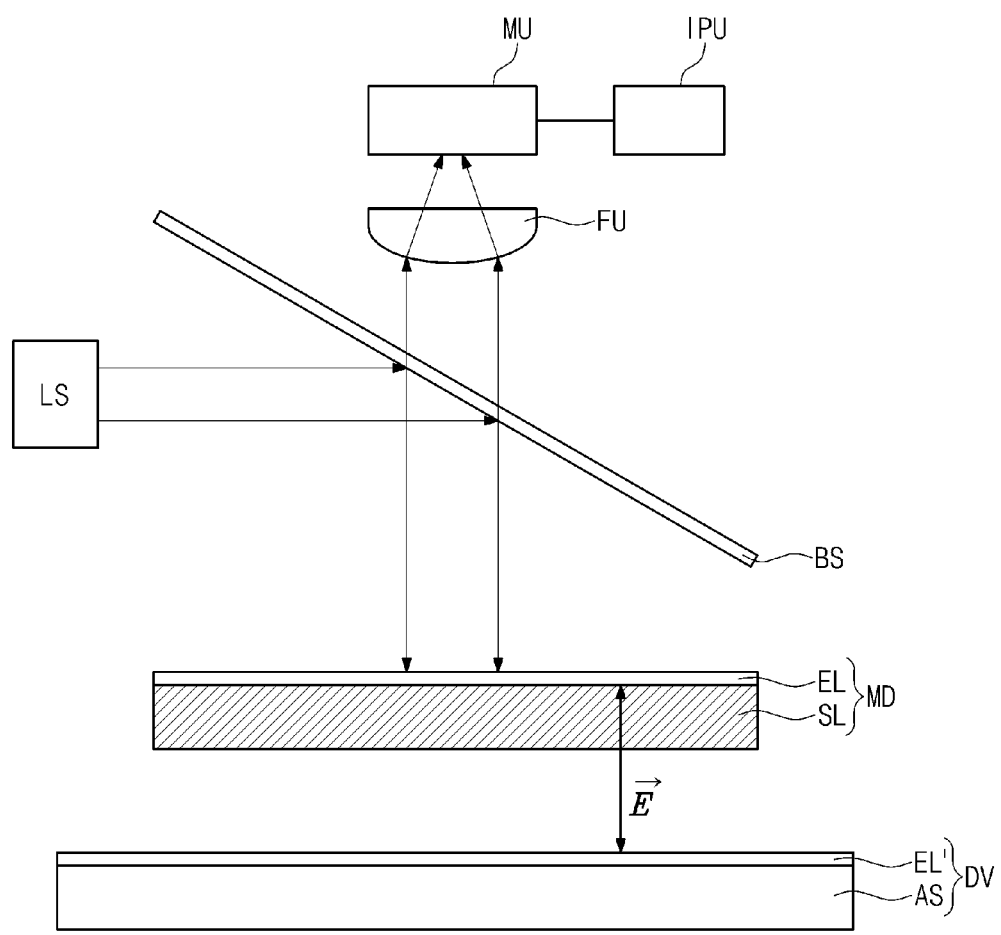
FIG. 1 illustrates an inspection apparatus according to an embodiment of the present inventive concept.

Embodiments of the present inventive concept will be described in detail with reference to the accompanying drawings. The inventive concept, however, may be embodied in various different forms, and should not be construed as being limited only to the illustrated embodiments. Rather, these embodiments are provided as examples so that this disclosure will be thorough and complete, and will fully convey the embodiments. Accordingly, known processes, elements, and techniques might not be described with respect to the exemplary embodiments. Unless otherwise noted, like reference numerals may refer to like elements throughout the attached drawings and written description, and thus descriptions might not be repeated. In the drawings, the sizes and relative sizes of layers and regions may be exaggerated for clarity.

It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the exemplary embodiment.

As used herein, the singular forms "a", "an" and "the" are intended to include the plural forms, unless the context clearly indicates otherwise.

FIG. 1 illustrates an inspection apparatus according to an embodiment of the present inventive concept, and FIG. 2 is a cross-sectional view of a liquid crystal modulator MD in FIG. 1.

Referring to FIGS. 1 and 2, an inspection apparatus may be an apparatus for detecting a defect of a display device (e.g., a defect of a display substrate DV used for the display device). However, the display device is not limited thereto. For example, the display device may include a liquid crystal display device, an electrowetting display device, an electrophoretic display device, an organic light emitting display device, etc.

In an embodiment, the display device may include a plurality of pixels. In an embodiment, the display device may further include an array substrate AS where a plurality of thin film transistors corresponding to the plurality of pixels are formed, a display substrate DV including electrodes connected to the thin film transistors, an opposite substrate (not shown) opposite to the display substrate DV, and an image display layer (not shown) disposed between the display substrate DV and the opposite substrate. In an embodiment, the display layer may be a liquid crystal layer of the liquid crystal display device, an electrowetting layer of the electrowetting display device, an electrophoretic layer of the electrophoretic display device, or an organic light emitting layer of the organic light emitting display device. The opposite substrate may be replaced with an encapsulation layer according to a type and a structure of the display device.

In an embodiment, the display substrate DV may include the array substrate AS and a target electrode EL' disposed on the array substrate AS. A plurality of target electrode EL' corresponding to the plurality of pixels may be provided.

Although not shown, the array substrate AS may include an insulating substrate and a plurality of driving circuits (e.g., thin film transistors) disposed on the insulating substrate. The driving circuits may be electrically connected to at least a portion of the target electrodes EL' to apply a predetermined voltage (e.g., about 10 volts) to the target electrode EL'.

Hereinafter, a configuration of the inspection apparatus will be described in more detail with an operating principle thereof.

The inspection apparatus according to an embodiment of the present inventive concept may include a light emitting unit LS, a beam splitter BS, a liquid crystal modulator MD, a focusing unit FU, a measurement unit MU, and an image processing unit IPU.

The light emitting unit LS outputs a light. In an embodiment, the light emitting unit LS may include various types of light sources such as a light emitting diode, a cold cathode fluorescence lamp, etc. Although not shown, the light emitting unit LS may include a light guide member such as a light guide plate to guide the light toward the beam splitter BS.

The beam splitter BS splits the light provided from the light emitting unit LS into a plurality of lights and provides the plurality of lights to the liquid crystal modulator MD. In an embodiment, the split lights may travel to different locations of the display substrate DV. In an embodiment, the split lights may be reflected by the liquid crystal modulator MD or the display substrate DV. When the split lights are reflected by the liquid crystal modulator MD, they may penetrate the beam splitter BS to be provided to the measurement unit MU. In an embodiment, each of the split lights may approximately correspond to each location of target electrodes EL'.

In an embodiment, the liquid crystal modulator MD may be a component for checking whether pixels of the display substrate DV are defective. In an embodiment, the liquid crystal modulator MD is disposed above the display substrate DV and is spaced apart from the display substrate DV. The transmittance or reflectance of the liquid crystal modulator MD varies depending on whether the display substrate DV is defective. Determination whether the pixels are defective is made based on the transmittance or the reflectance of the liquid crystal modulator MD. In an embodiment, the liquid crystal modulator MD may include an electrode EL (hereinafter referred to as "an opposite electrode") and a sensor layer SL. The sensor layer may be the same as a liquid crystal layer throughout the specification.

Referring to FIG. 2, the liquid crystal modulator MD includes a first substrate SUB1, a second substrate SUB2, a reflection layer RFL, an opposite electrode EL, a sensor layer SL, and a polarizer POL. The reflection layer RFL may be disposed on an upper surface of the substrate SUB1. The opposite electrode EL may be disposed on a lower surface of the second substrate SUB2. The sensor layer SL may be disposed between an upper surface of the reflection layer RFL and a lower surface of the opposite electrode EL. The polarizer POL may be attached to an upper surface of the second substrate SUB2 with an adhesive layer ADH interposed therebetween.

More specifically, the sensor layer SL may be attached to an upper surface of the reflection layer RFL with a first alignment layer ALN1 interposed therebetween, the opposite electrode EL may be attached to an upper surface of the sensor layer SL with an insulating layer INS and a second alignment layer ALN2 interposed between the opposite electrode EL and the sensor layer SL, the second substrate SUB2 may be disposed on an upper surface of the opposite electrode EL, and the polarizer POL may be disposed depending on the stacked order. A third substrate SUB3 may be disposed between the second substrate SUB2 and an anti-reflection layer AG and may be disposed on an upper surface of the polarizer POL. The anti-reflection layer AG may be disposed on an upper surface of the third substrate SUB3.

In an embodiment, the first substrate SUB1 may be a transparent insulation substrate and may be made of materials such as quartz, glass, plastic, etc.

In an embodiment, the reflection layer RFL may reflect light that is provided from the beam splitter BS and travels in the liquid crystal layer. A wavelength of the light reflected by the reflection layer RFL may vary depending on a wavelength of a light sensed in the measurement unit MU that will be explained later. In an embodiment, the wavelength of the light reflected by the reflection layer RFL may be between about 380 nanometers and about 700 nanometers.

In an embodiment, the reflection layer RFL may include a metal layer or a dielectric mirror. However, the reflection layer RFL is not limited thereto and may include any type of components that reflects light.

The dielectric mirror includes a plurality of dielectric layers having different refractive indices. For example, the dielectric mirror may include a first dielectric layer having a first refractive index and a second dielectric layer having a second refractive index. The first and second dielectric layers may be arranged alternately one or more times. The first refractive index and the second refractive index may be different from each other, and dielectric constants of the first and second dielectric layers may be about 7 or less.

In an embodiment, the first dielectric layer may include zirconium oxide and the second dielectric layer may include silicon oxide. In an embodiment, a refractive index of the zirconium oxide may be between about 1.34 and about 1.46 and a refractive index of the silicon oxide may be between about 1.67 and about 1.72. In an embodiment, the first dielectric layer may include zirconium oxide and the second dielectric layer may include titanium oxide.

The sum total of the first and second dielectric layers may be three or more. In an embodiment, the sum total of the first and second dielectric layers may be 15 or more.

The second substrate SUB2 may be a transparent insulation substrate and may be made of materials such as quartz, glass, plastic, etc.

A predetermined level of voltage (e.g., about 150 volts to 350 volts) may be applied to the opposite electrode EL, and thus, an electric field may be established together with the target electrode EL'. The opposite electrode EL may be made of a transparent conductive material such as an indium tin oxide (ITO), an indium zinc oxide (IZO), an indium tin zinc oxide (ITZO), a conductive polymer, etc.

An insulating layer INS may be provided between the opposite electrode EL and the sensor layer SL to protect the opposite electrode EL and to separate the opposite electrode EL and the sensor layer SL from each other. The insulating layer INS may be omitted.

A transmittance of the sensor layer SL varies depending on the electric field established between the opposite electrode EL and the target electrode EL'. The sensor layer SL may be made of a liquid crystal.

A first alignment layer ALN1 and a second alignment layer ALN2 may be provided in the liquid crystal modulator MD to perform pre-alignment on the liquid crystal of the liquid crystal modulator MD. The first alignment layer ALN1 may be provided between the reflection layer RFL and the sensor layer SL. The second alignment layer ALN2 may be provided between the sensor layer SL and the opposite electrode EL. One of the first and second alignment layers ALN1 and ALN2 may be a vertical alignment layer and the other alignment layer may be a horizontal alignment layer. The vertical alignment layer is provided to vertically pretilt liquid crystals near the vertical alignment layer with respect to a plane on which the vertical alignment layer is disposed. The horizontal alignment layer is provided to horizontally pretilt liquid crystals near the horizontal alignment layers with respect to a plane on which the horizontal alignment layer is disposed. In an embodiment, a pre-tilt angle of the vertical alignment layer may be between about 89 degrees and about 90 degrees, and a pre-tilt angle of the horizontal alignment layer may be between about zero degree and about two degrees. In an embodiment, the first alignment layer ALN1 may be a horizontal alignment layer and the second alignment layer ALN2 may be a vertical alignment layer. In an embodiment, the first alignment layer ALN1 may be a vertical alignment layer and the second alignment layer ALN2 may be a horizontal alignment layer. The horizontal alignment layer may have a rubbing axis titled at an angle of about 45 degrees with respect to an optical axis of the polarizer POL that will be explained later.

The liquid crystal layer includes a hybrid aligned nematic (HAN) liquid crystal. For example, the sensor layer SL includes HAN liquid crystal molecules whose pre-tilt angle gradually increases from the first alignment layer ALN1 to the second alignment layer ALN2. Thus, the liquid crystal molecules near the first alignment layer ALN1 may be arranged to be substantially horizontal to a surface of the first substrate SUB1 and liquid crystal molecules near the second alignment layer ALN2 may be arranged to be substantially vertical to a surface of the second substrate SUB2.

A distance between the first alignment layer ALN1 and the second alignment layer ALN2 (i.e., cell gap) may be set such that the HAN liquid crystal delays one of polarization components of light passing through the liquid crystal layer with respect to the other polarization component by a quarter wavelength of the light. For example, an amount of retardation between two polarization components of the light through the liquid crystal layer may be between about 125 nanometers and about 140 nanometers when a wavelength of the light is about 550 nanometers. An amount of retardation between two polarization components of the light through the sensor layer SL may be between about 160 nanometers and about 170 nanometers when a wavelength of the light is about 600 nanometers. In an embodiment, the cell gap may be between about 3 micrometers and about 8 micrometers.

Liquid crystal molecules constituting the liquid crystal layer may have positive dielectric anisotropy. Refractive index anisotropy of the liquid crystal molecules may be between about 0.8 and about 0.3, and dielectric anisotropy of the liquid crystal molecules may be between about 3 and about 15.

The polarizer POL may be attached to a top surface of the second substrate SUB2 with an adhesive ADH interposed therebetween. The polarizer POL has a polarizing axis such that a light incident to the beam splitter BS and a light emitted from the beam splitter BS have a predetermined polarizing direction.

A third substrate SUB3 may be provided on a surface of the polarizer POL to support and protect components such as the first substrate SUB1, the second substrate SUB2, and the liquid crystal layer.

The adhesive ADH may be provided between the second substrate SUB2 and the third substrate SUB3 and may tightly bond the second and third substrates SUB2 and SUB3 to each other. The third substrate SUB3 may be made of an optically transparent material such as quartz, glass, plastic, etc. In an embodiment, the third substrate SUB3 may be made of quartz or glass. The third substrate SUB3 supports and protects underlying components (e.g., the first substrate SUB1, the sensor layer SL, the second substrate SUB2, etc).

In an embodiment, an anti-reflection layer AG may be provided on the third substrate SUB3. The anti-reflection layer AG may be provided on an upper surface of a transparent substrate SUB facing the beam splitter. In an embodiment, the anti-reflection layer AG may be omitted.

The focusing unit FU is disposed between the beam splitter BS and the measurement unit MU. The focusing unit FU focuses the split light reflected by the liquid crystal modulator MD. In an embodiment, the focusing unit FU may be a lens having a convex surface.

The split lights focused by the focusing unit FU are provided to the measurement unit MU. In an embodiment, the measurement unit MU may include a plurality of charge-coupled devices (CCDs). The measurement unit MU may generate data signals each corresponding to light intensity of each of the split lights using the CCDs. In an embodiment, each of the split lights may be provided to a corresponding CCD.

The image processing unit IPU converts the data signals generated by the measurement unit MU into images. Thus, an operator may determine whether each pixel electrode is defective based on the images displayed through the image processing unit IPU.

The above-configured liquid crystal modulator may be driven in a normally black mode. Hereinafter, a method of operating an inspection apparatus according to an embodiment of the present inventive concept in a normally black mode will be described.

Figure 3A:
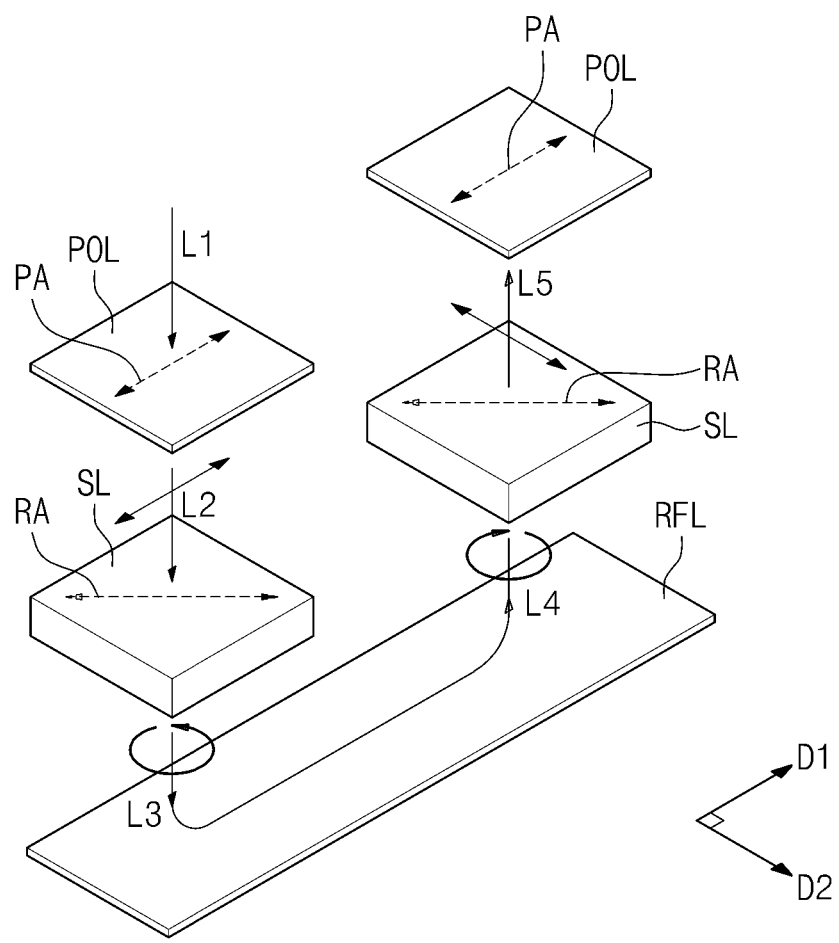
Figure 3B:
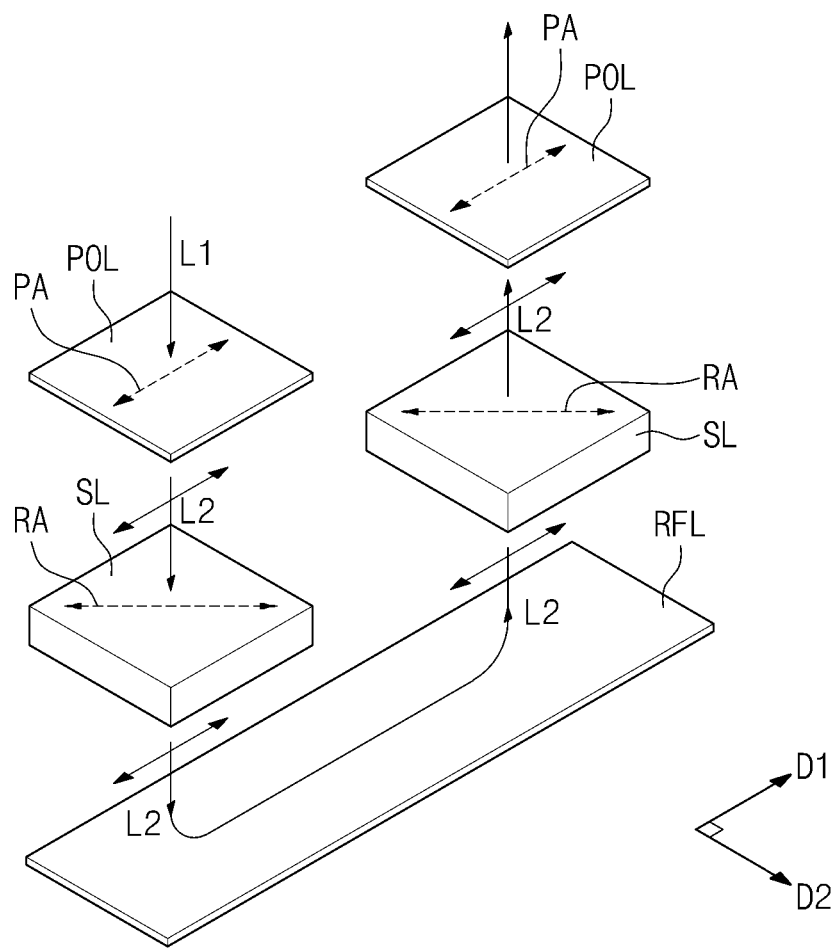

FIGS. 3A and 3B are perspective views illustrating that an inspection apparatus according to an embodiment of the present inventive concept is driven in a normally black mode. FIG. 3A shows a case when a voltage is not applied to a liquid crystal modulator and FIG. 3B shows a case when a voltage is applied to a liquid crystal modulator. In FIGS. 3A and 3B, although a polarizer POL and a sensor layer SL are separately shown, they may be formed as part of a single device.

Figure 4A:
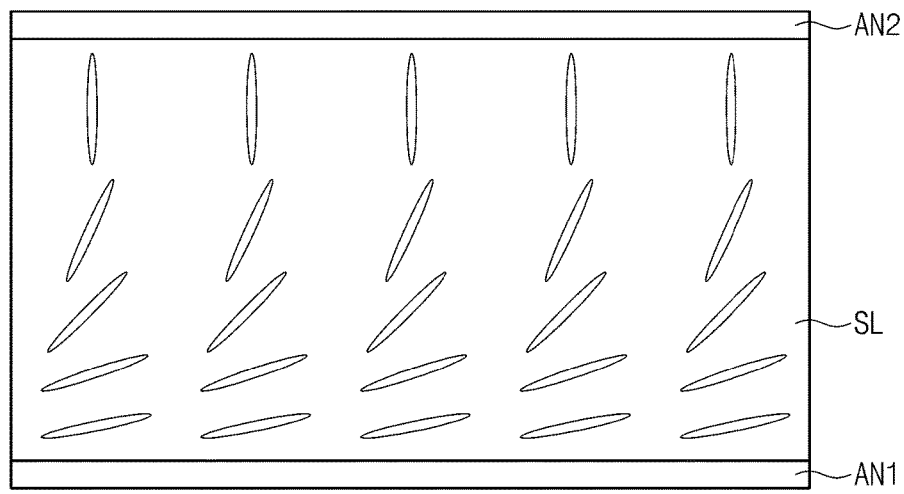
FIGS. 4A and 4B are cross-sectional views showing a sensor layer, a first alignment layer, and a second alignment layer when a voltage is not applied to each sensor layer and when a voltage is applied to each sensor layer, respectively.
Figure 4B:
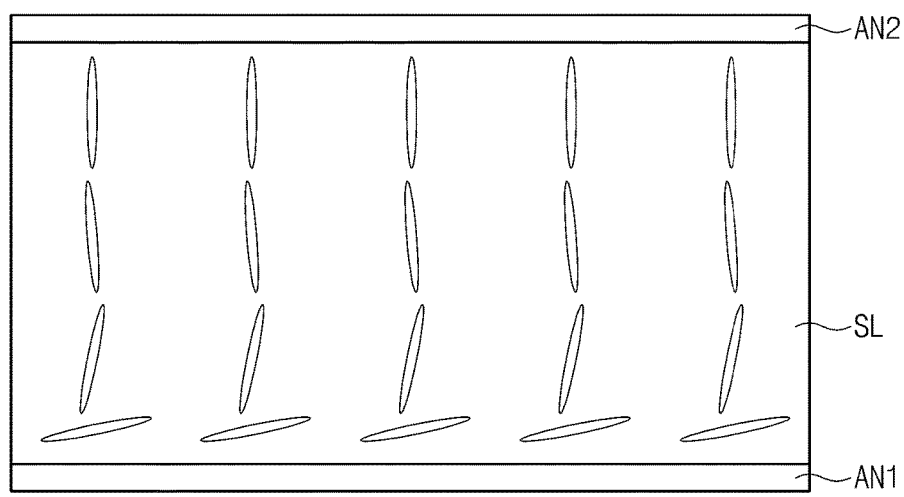

FIGS. 4A and 4B are cross-sectional views showing a sensor layer SL, a first alignment layer ALN1, and a second alignment layer ALN2. FIG. 4A illustrates a case when a voltage is not applied to each sensor layer and FIG. 4B illustrates a case when a voltage is applied to each sensor layer.

Referring to FIGS. 3A and 4A, a light emitted from a light source is referred to as a first light L1 and the first light L1 turns into a second light L2 after passing through a polarizer POL having a polarizing axis PA of a first direction D1. The first light L1 does not have a specific polarizing direction when it is emitted from the light source. The first light L1 turns into the second light L2 that is linearly polarized in the first direction D1 after passing through the polarizer POL.

The second light L2 turns into a third light L3 after passing through the sensor layer SL. The sensor layer SL is not supplied with a voltage, and liquid crystal molecules of the sensor layer SL are arranged to be horizontal to a first substrate SUB1 along a rubbing axis RA in the vicinity of a first alignment layer ALN1 (e.g., a horizontal alignment layer). The rubbing axis RA may have a direction tilted to a direction of a polarizing axis PA of the polarizer POL. For example, when the polarizer POL has the polarizing axis PA of the first direction D1 as shown in FIG. 3A, the rubbing axis RA may be a direction titled at an angle of about 45 degrees with respect to the first direction D1. The liquid crystal molecules of the sensor layer SL are arranged to be vertical to a second direction D2 in the vicinity of a second alignment layer ALN2 (e.g., a vertical alignment layer). Accordingly, the liquid crystal molecules of the sensor layer SL have an arrangement where an amount of pretilt angle to the first or second substrate increases as the liquid crystal molecules get closer to the second alignment layer ALN2 from the first alignment layer ALN1. Thus, a phase of one of polarization components of the second light L2 is delayed to the other polarization component by a quarter wavelength when the second light L2 passes through the sensor layer SL. As a result, the third light L3 is circularly polarized in a specific direction (e.g., clockwise direction or counterclockwise direction).

The circularly polarized third light L3 is reflected at the reflection layer RFL to turn into a fourth light L4. The fourth light L4 is circularly polarized in a direction opposite to the direction of the third light L3. For example, when the third light L3 is circularly polarized in the clockwise direction, the fourth light L4 is circularly polarized in the counterclockwise direction. When the third light L3 is circularly polarized in the counterclockwise direction, the fourth light L4 is circularly polarized in the clockwise direction.

If the fourth light L4 passes through the sensor layer SL, a phase of polarization components of the fourth light L4 is delayed by a quarter wavelength and thus, the circularly polarized fourth light L4 turns into a fifth light L5 that is linearly polarized in the second direction D2. The second direction D2 is orthogonal to the first direction D1.

Since the fifth light L5 is linearly polarized in a direction orthogonal to the polarizing axis PA of the polarizer POL, the fifth light L5 might not pass through the polarizer POL and might not travel to the focusing unit FU. Thus, a liquid crystal modulator may have a black output.

Referring to FIGS. 3B and 4B, a first light L1 emitted from a light source turns to a second light L2 after passing through a polarizer POL having a polarizing axis PA of a first direction D1. The first light L1 does not have a specific polarizing direction when it is emitted from the light source. The first light L1 turns into the second light L2 that is linearly polarized in the first direction after passing through the polarizer POL.

Next, the second light L2 passes through the sensor layer SL. The sensor layer SL is supplied with a voltage, and liquid crystal molecules of the sensor layer SL are arranged along an electric field established by the applied voltage. Since the liquid crystal molecules may have positive dielectric anisotropy, they are arranged in a direction orthogonal to a first substrate SUB1, as shown in FIG. 4B. However, at a portion adjacent to the first alignment layer ALN1, an alignment force generated by the first alignment layer ALN1 may be greater than a force generated by the applied electric field. Thus, liquid crystal molecules near the first alignment layer ALN1 may remain in an original state (e.g., horizontally arranged state).

Since the second light L2 passes through the liquid crystal molecules arranged in a vertical direction, a phase delay between the polarization components of the second light L2 might not occur. For example, since a phase delay between the polarization components of the second light L2 might not occur, the same numeral L2 may be used to represent the light that passes through the sensor layer SL.

Next, the second light L2 is reflected at a reflection layer RFL and remains in a linearly polarized state in the first direction D1. The second light L2 remains in the linearly polarized state in the first direction D1 even after being reflected at the reflection layer RFL. In addition, since a phase delay between the polarization components does not occur when the second light L2 passes through the sensor layer SL, the sensor layer SL remains in a linearly polarized state in the first direction D1.

Since the second light L2 incident to the polarizer POL is linearly polarized in the same direction as the polarizing axis of the polarizer POL, the second light L2 may pass through the polarizer POL and may travel to a focusing unit. As a result, the liquid crystal modulator may have a white output.

The above-structured liquid crystal modulator may have black and white outputs corresponding to a defective pixel and a normal pixel, respectively. For example, the liquid crystal modulator may have the black output as shown in FIG. 3A because a target electrode EL' might not be supplied with a voltage when a driving circuit or the target electrode EL' among pixels of the display substrate is defective. The liquid crystal modulator may have the white output, as shown in FIG. 3B, because a target electrode EL' may be supplied with a voltage when pixels of the display substrate are non-defective.

Figure 5:
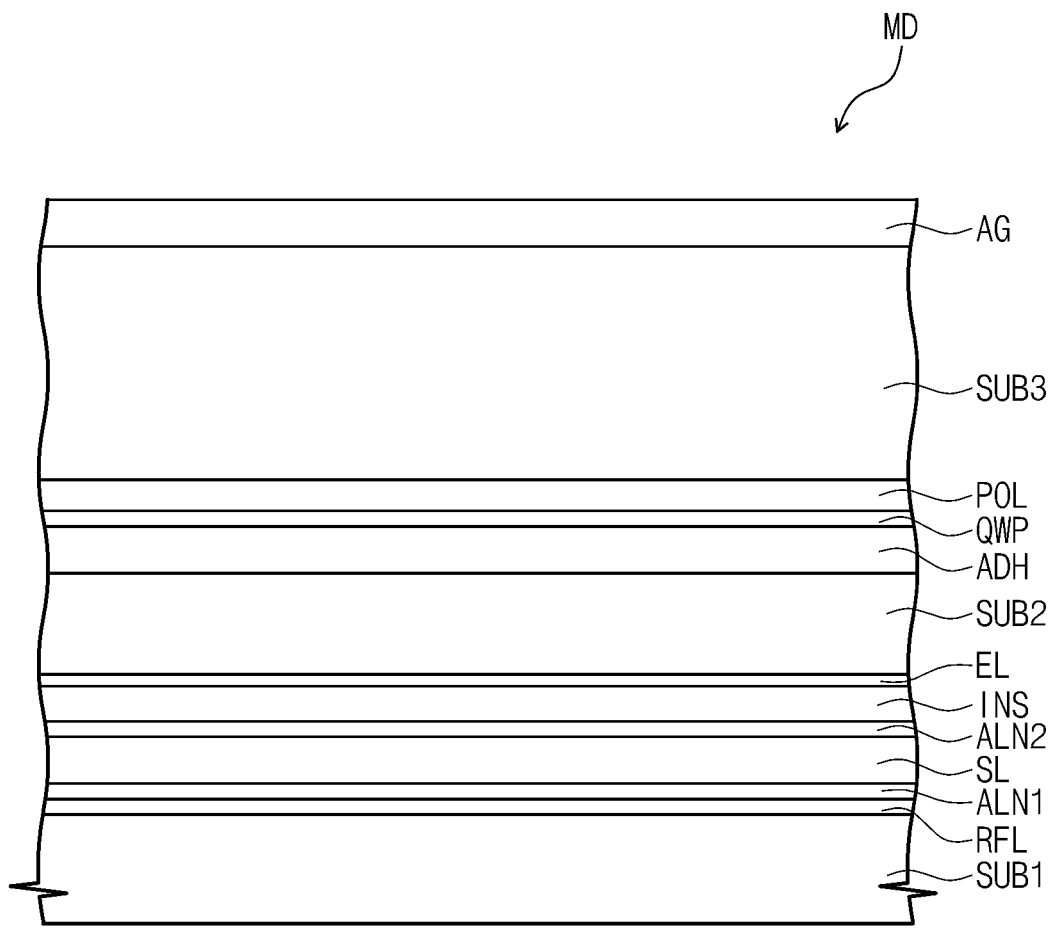
FIG. 5 is a cross-sectional view of a liquid crystal modulator according to an embodiment of the present inventive concept.

FIG. 5 is a cross-sectional view of a liquid crystal modulator MD according to an embodiment. In a display device according to an exemplary embodiment of the present inventive concept, for convenience of description, the following description will focus on differences from the previous exemplary embodiment and omitted parts may be similar to similar parts discussed above with respect to previous exemplary embodiment.

Referring to FIG. 5, the liquid crystal modulator MD includes a first substrate SUB1, a second substrate SUB2, a reflection layer RFL, an opposite electrode EL, a sensor layer SL, a quarter wave plate QWP, and a polarizer POL. The reflection layer RFL may be disposed on an upper surface of the substrate SUB1. The opposite electrode EL may be disposed on a lower surface of the second substrate SUB2. The sensor layer SL may be disposed between an upper surface of the reflection layer RFL and a lower surface of the opposite electrode EL. The quarter wave plate QWP may be attached to an upper surface of the second substrate SUB2 with an adhesive layer ADH interposed therebetween. The polarizer POL may be disposed on an upper surface of the quarter wave plate QWP.

More specifically, the sensor layer SL may be attached to an upper surface of the reflection layer RFL with a first alignment layer ALN1 interposed therebetween, the opposite electrode EL may be attached to an upper surface of the sensor layer SL with an insulating layer INS and a second alignment layer ALN2 interposed between the opposite electrode EL and the sensor layer SL, the second substrate SUB2 may be disposed on an upper surface of the opposite electrode EL, and the quarter wave plate QWP and the polarizer POL may be disposed according to a stacked order. A third substrate SUB3 may be disposed between the second substrate SUB2 and an anti-reflection layer AG and may be disposed on an upper surface of the polarizer POL. The anti-reflection layer AG may be disposed on an upper surface of the third substrate SUB3.

The polarizer POL has a polarizing axis PA such that a light incident to the beam splitter BS and a light emitted from the beam splitter BS have a predetermined polarized direction.

The quarter wave plate QWP may be an optical film to delay a phase of a polarization component at slow axis of a light passing through the quarter wave plate QWP by a quarter wavelength of the light and thus, may have an optical axis OA titled to the polarizing axis PA of the polarizer POL. For example, if the polarizer POL has a polarizing axis PA of a first direction, the quarter wave plate QWP may have an optical axis OA titled at an angle of about 45 degrees to the first direction. In this case, the optical axis OA of the quarter wave plate QWP may have the substantially same direction as a rubbing axis RA of a horizontal alignment layer. Alternatively, the optical axis OA may have the substantially vertical direction to the rubbing axis RA of the horizontal alignment layer The above-structured liquid crystal modulator may be driven in a normally white mode. Hereinafter, a method of operating an inspection apparatus according to an embodiment of the present inventive concept in a normally white mode will be described.

Figure 6A:
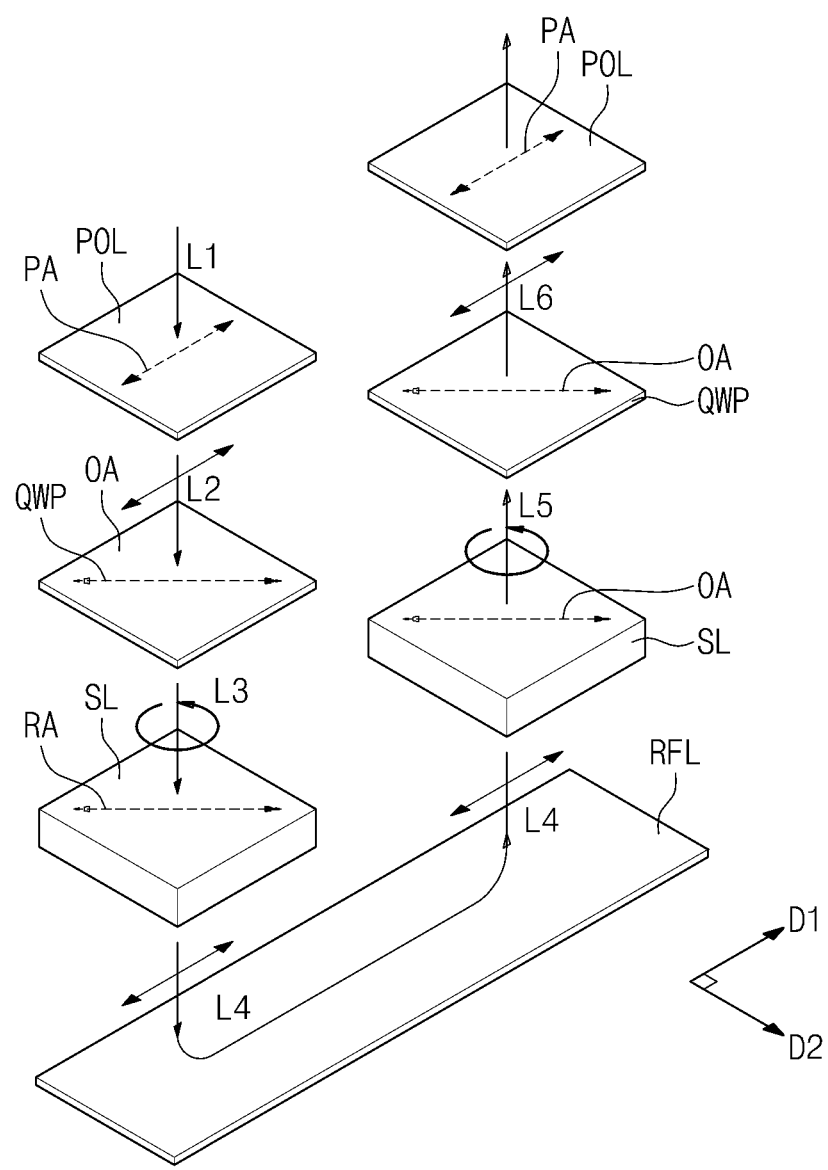
Figure 6B:
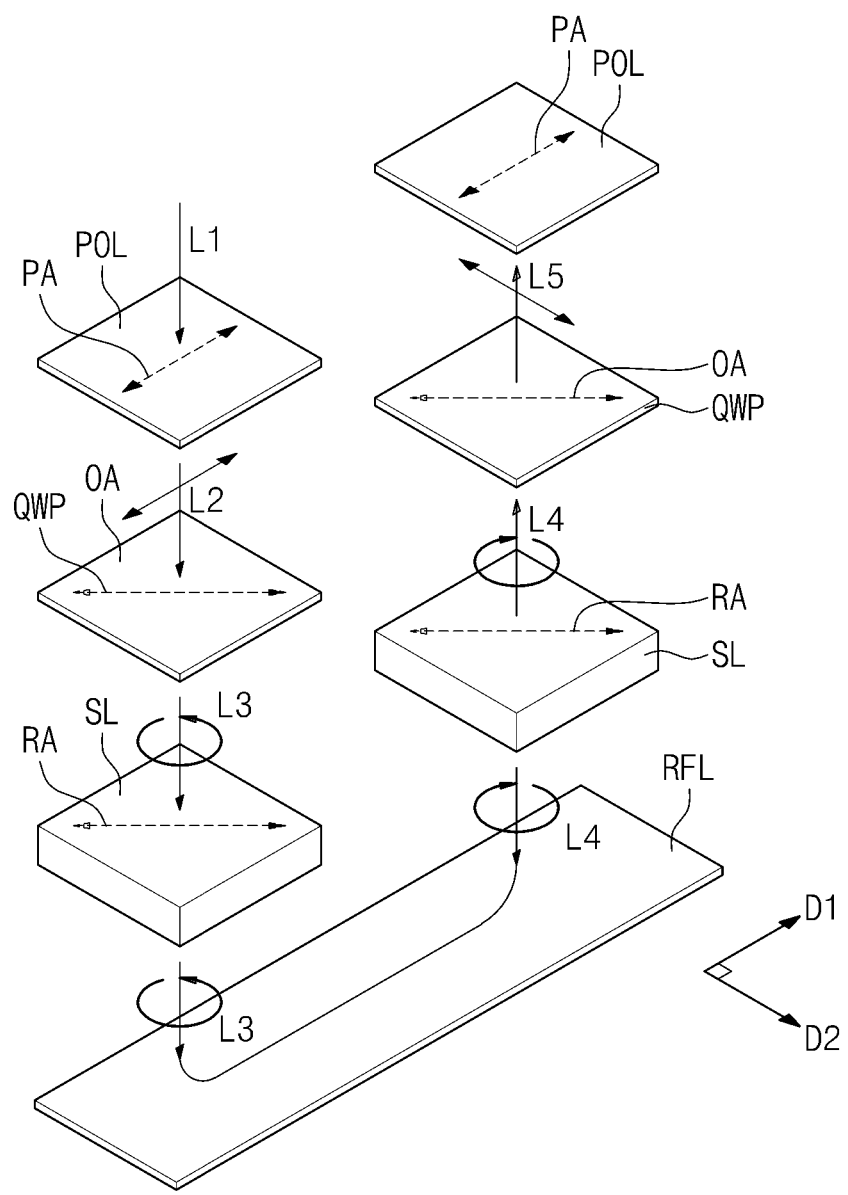

FIGS. 6A and 6B are perspective views illustrating that an inspection apparatus according to an embodiment of the present inventive concept is driven in a normally white mode. FIG. 6A shows a case when a voltage is not applied to a liquid crystal modulator and FIG. 6B shows a case when a voltage is applied to a liquid crystal modulator. In FIGS. 6A and 6B, for convenience of description, other components are omitted other than a sensor layer SL, a quarter wave plate QWP, and a reflection layer RFL. Although, a polarizer POL, the quarter wave plate QWP, and the sensor layer SL are separately shown according to a traveling path of light, they may be formed as part of a single device.

Referring to FIG. 6A, if a light emitted from a light source is referred to as a first light L1, the first light L1 turns into a second light L2 after passing through the polarizer POL having a polarizing axis PA of a first direction D1. The first light L1 does not have a specific polarizing direction when it is emitted from a light source. The first light L1 turns into the second light L2 that is linearly polarized in the first direction after passing through the polarizer POL.

The second light L2 turns into a third light L3 after passing through the quarter wave plate QWP. Since the quarter wave plate QWP delays a phase of a polarization component at slow axis of a light passing through the quarter wave plate QWP by a quarter wavelength, the second light L2 turns into the third light L3 that is a circularly polarized light in a direction (e.g., clockwise direction or counterclockwise direction) after passing through the quarter wave plate QWP.

The third light L3 passes through the sensor layer SL. Since the sensor layer SL is not supplied with a voltage, liquid crystal molecules of the sensor layer SL are arranged to be horizontal to a first substrate SUB1 along a rubbing axis in the vicinity of a first alignment layer ALN1 (e.g., a horizontal alignment layer) and are arranged to be vertical to a second direction SUB2 in the vicinity of a second alignment layer ALN2 (e.g., a vertical alignment layer), as illustrated in FIG. 4A. For example, the liquid crystal molecules of the sensor layer SL have an arrangement where an amount of pretilt angle to the first or second substrate increases as the liquid crystal molecules get closer to the second alignment layer ALN2 from the first alignment layer ALN1. Thus, the third layer L3 turns into a fourth light L4 linearly polarized in the same direction (i.e., first direction D1) as the second light L2 because a phase of the third light L3 is delayed after the third light L3 passes through the sensor layer SL.

The linearly polarized fourth light L4 is reflected at a reflection layer RFL and remains in a linearly polarized state in the first direction D1.

The fourth light L4 reflected at the reflection layer RFL turns into a fifth light L5 after passing through the sensor layer SL. Since the sensor layer SL is not supplied with a voltage, a phase delay of a quarter wavelength between the polarization components of the fourth light L4 occur when the fourth light L4 passes through the sensor layer SL. As a result, the fourth light L4 turns into the fifth light L5 circularly polarized in a specific direction (e.g., clockwise direction or counterclockwise direction). The fifth light L5 is circularly polarized in the same direction as the third light L3.

The fifth light L5 turns into a sixth light L6 after passing through the quarter wave plate QWP. Since the quarter wave plate QWP delays a phase of a polarization component at slow axis of a light passing through the quarter wave plate QWP by a quarter wavelength, the fifth light L5 turns into the sixth light L6 linearly polarized in the first direction D1 after passing through the quarter wave plate QWP.

Since the sixth light L6 is linearly polarized in the same direction as the polarizing axis PA of the polarizer POL, the sixth light L6 travels in a direction of a focusing unit FU after passing through the polarizer POL. As a result, a liquid crystal modulator may have a white output.

Referring to FIG. 6B, if a light emitted from a light source is referred to as a first light L1, the first light L1 turns into a second light after passing through the polarizer POL having a polarizing axis PA of the first direction D1. The first light L1 does not have a specific polarizing direction when it is emitted from the light source. The first light L1 turns into the second light L2 that is linearly polarized in the first direction after passing through the polarizer POL.

The second light L2 turns into a third light L3 after passing through the quarter wave plate QWP. Since the quarter wave plate QWP delays a phase of a polarization component at slow axis of a light passing through the quarter wave plate QWP by a quarter wavelength, the second light L2 turns into the third light L3 circularly polarized in a direction (e.g., clockwise direction or counterclockwise direction) after passing through the quarter wave plate QWP.

The third light L3 passes through a sensor layer SL. The sensor layer SL is supplied with a voltage, and liquid crystal molecules of the sensor layer SL may be arranged along an electric field established by the supplied voltage. Since the liquid crystal molecules may have positive dielectric anisotropy, they are arranged in a direction orthogonal to a first substrate SUB1. Since the third light L3 passes through the vertically arranged liquid crystal molecules, polarization components of the third light L3 may have the substantially same velocity over the sensor layer SL and thus, the phase difference between the polarization components might not be changed.

The circularly polarized third light L3 is reflected at a reflection layer RFL to turn into a fourth light L4 circularly polarized in a direction opposite to a direction of the third light L3. For example, when the third light L4 is circularly polarized in the clockwise direction, the fourth light L4 is circularly polarized in the counterclockwise direction. On the other hand, when the third light L3 is circularly polarized in the counterclockwise direction, the fourth light L4 is circularly polarized in the clockwise direction.

The fourth light L4 passes through the sensor layer SL. The phase difference between the polarization components of the fourth light L4 might not be changed. For example, since phases of the polarization components of the fourth light L4 might not be changed, the same numeral L4 may be used to represent the light that passes through the sensor layer SL.

The fourth light L4 turns into a fifth light L5 after passing through the quarter wave plate QWP. Since the quarter wave plate QWP delays a phase of a polarization component at slow axis of a light passing through the quarter wave plate QWP by a quarter wavelength, the fourth light L4 turns into the fifth light L5 linearly polarized in the second direction D2 after passing through the quarter wave plate QWP.

Thus, since the fifth light L5 has an optical axis orthogonal to a polarizing axis PA of the polarizer POL, the fifth light L5 might not pass the polarizer POL and might not travel to a focusing unit FU. As a result, a liquid crystal modulator may have a black output.

The above-structured liquid crystal modulator may have black and white outputs corresponding to a defective pixel and a normal pixel, respectively. For example, the liquid crystal modulator may have the black output as shown in FIG. 6A because a target electrode EL' might not be supplied with a voltage when a driving circuit or the target electrode EL' among pixels of the display substrate is defective. The liquid crystal modulator may have the white output, as shown in FIG. 6B, because a target electrode EL' may be supplied with a voltage when pixels of the display substrate are non-defective.

Figure 7A:
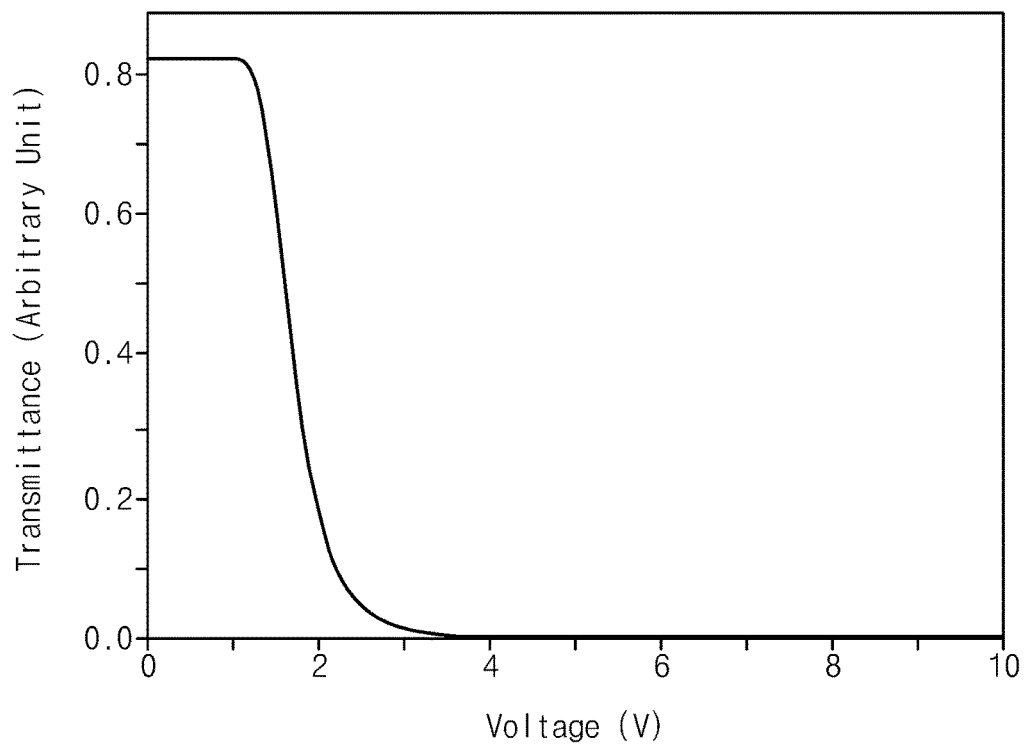
Figure 7B:
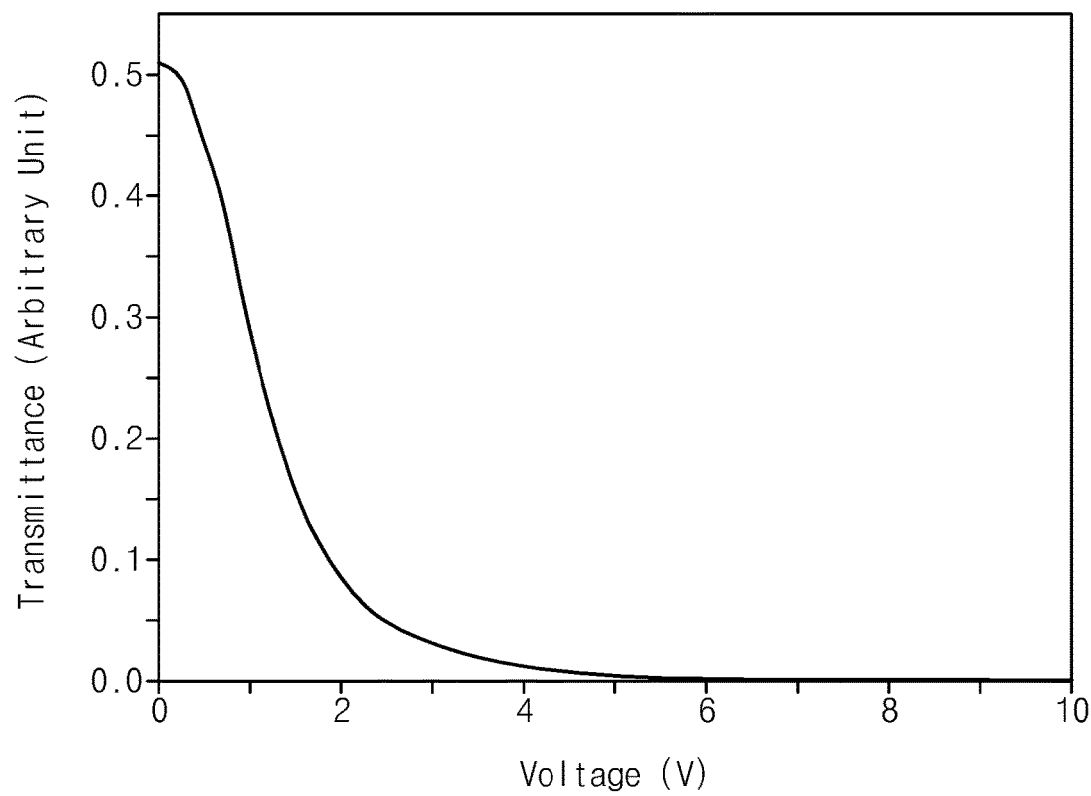

FIGS. 7A and 7B show voltage-dependent transmittances when a conventional liquid crystal modulator and a liquid crystal modulator according to an embodiment of the present inventive concept are used, respectively. FIG. 7A is a graph of a voltage-dependent transmittance when a TN mode liquid crystal is adopted and FIG. 7B is a graph of a voltage-dependent transmittance when a HAN mode liquid crystal according to an embodiment of the present inventive concept is adopted. In the liquid crystal modulators in FIGS. 7A and 7B, other than a liquid crystal and an alignment layer, the other components were manufactured under the same condition. When a TN mode liquid crystal modulator was manufactured, a delay value, i.e., d(cell gap)×refractive-index anisotropy (Δn) was 0.48 micrometer. When an HAN mode liquid crystal modulator was manufactured, delay value, i.e., d(cell gap)×refractive-index anisotropy (Δn) was 0.33 micrometer.

Referring to FIGS. 7A and 7B, a driving voltage of a conventional TN mode liquid crystal modulator was about 2.3 volts, and a driving voltage of an HAN mode liquid crystal modulator according to an embodiment of the present inventive concept was about 2.6 volts. That is, similar values were exhibited in both modes. Thus, the liquid crystal modulator according to an embodiment of the present inventive concept may also be easily driven by a similar level of driving voltage to the TN mode liquid crystal modulator.

Figure 8A:
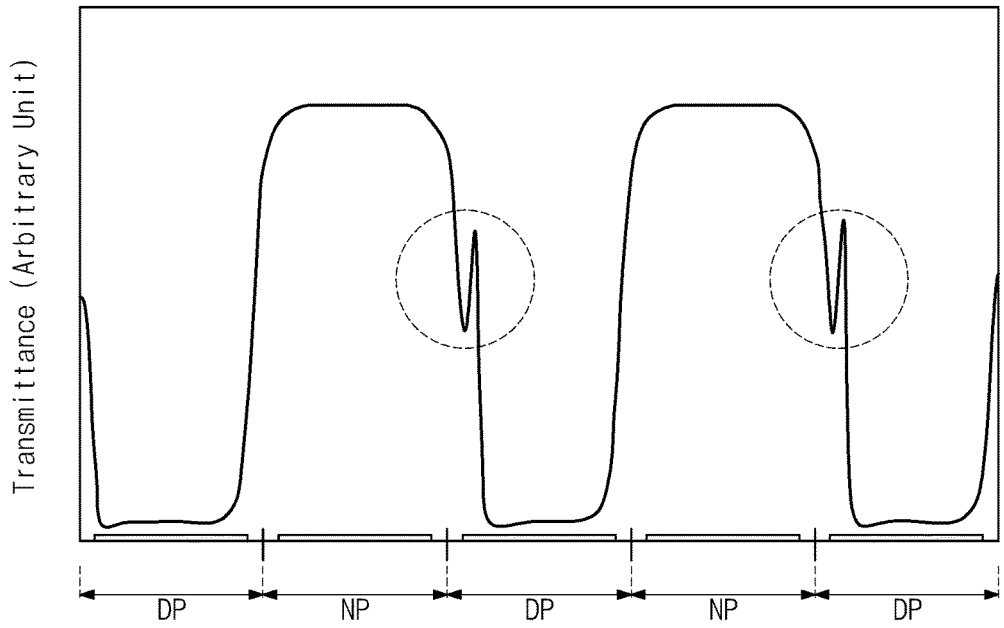
Figure 8B:
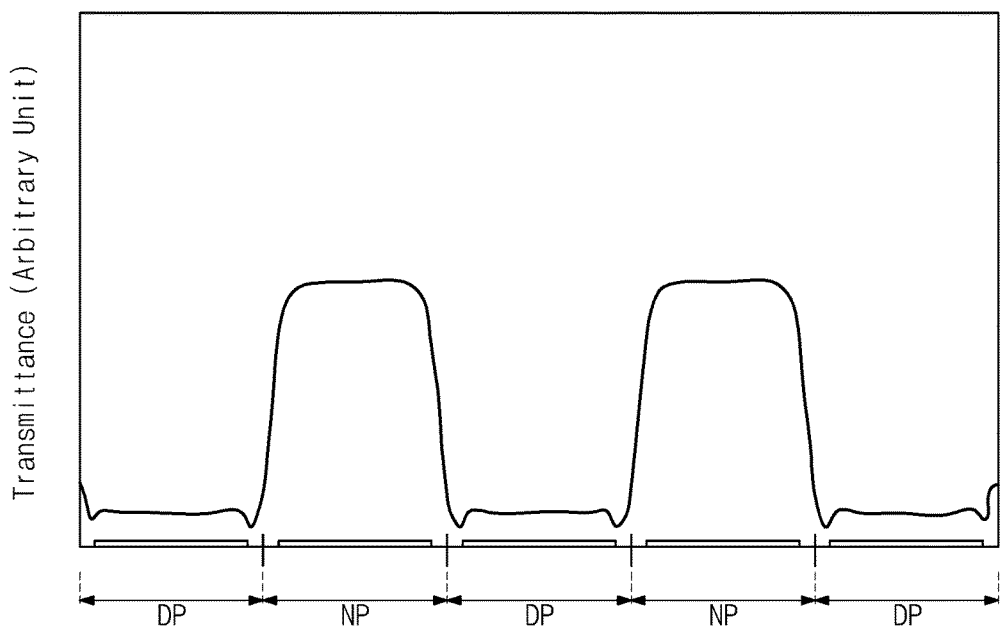

FIGS. 8A and 8B show transmittances depending on a pixel configuration when a conventional liquid crystal modulator and a liquid crystal modulator according to an embodiment of the present inventive concept are used, respectively. FIG. 8A is a graph of a transmittance when a TN mode liquid crystal is adopted and FIG. 8B is a graph of a transmittance when a HAN mode liquid crystal according to an embodiment of present inventive concept is adopted. In the liquid crystal modulators in FIGS. 8A and 8B, after pixels are sequentially arranged and alternately supplied with voltages, transmittances depending on a series of pixels were measured. A pixel supplied with a voltage indicates a normal pixel, and a pixel not supplied with a voltage indicates a defective pixel. Other than a liquid crystal and an alignment layer, the other components were manufactured under the same condition.

Referring to FIGS. 8A and 8B, in case of a conventional liquid crystal modulator adopting a TN mode, an abnormally transmitted portion of light (circular portion indicated by dotted lines) is discovered between a normal pixel and a defective pixel. However, in case of a liquid crystal modulator adopting an HAN mode according to an embodiment of present inventive concept, there is no abnormally transmitted portion of light between a normal pixel and a defective pixel. Liquid crystal molecules in the TN mode may be twisted in the early stage, but may be vertically arranged after being supplied with a voltage. Liquid crystal molecules in the HAN mode may be vertically aligned in the early stage, but may be entirely vertically arranged after being supplied with a voltage. Since vertical arrangement speed of the liquid crystal molecules in the HAN mode is high after they are supplied with a voltage, elastic energy may be reduced at the boundary between a normal pixel and a defective pixel. Thus, an abnormally transmitted portion may be reduced or might not exist.

Figure 9:
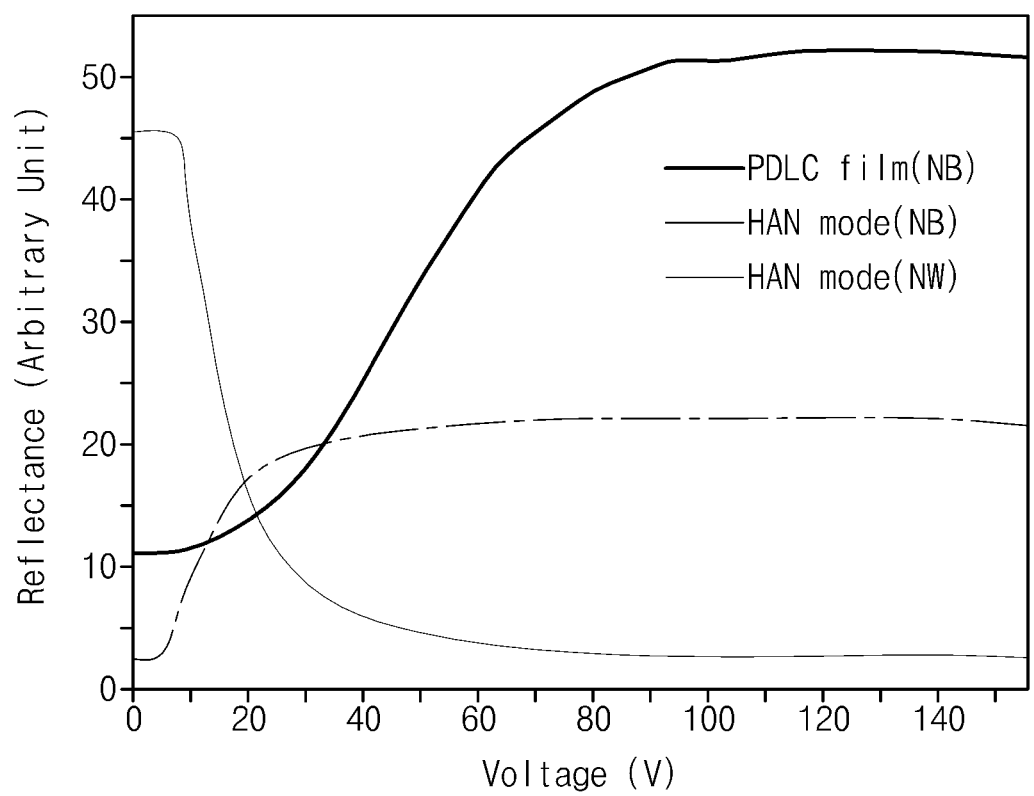
FIG. 9 shows reflectances depending on an applied voltage when a conventional liquid crystal modulator and a liquid crystal modulator according to an embodiment of the present inventive concept are used.

FIG. 9 shows reflectances depending on an applied voltage when a conventional liquid crystal modulator and a liquid crystal modulator according to an embodiment of the present inventive concept are used. In FIG. 9, a portion indicated by "PDLC film (NB)" means a liquid crystal modulator, driven in a normally black mode, where a polymer dispersed liquid crystal is adopted to a sensor layer. A portion indicated by "HAN mode (NB)" means a liquid crystal modulator according to an embodiment of the present inventive concept (e.g., a liquid crystal modulator driven in a normally white mode).

Referring to FIG. 9, in case of a liquid crystal modulator adopting a PDLC film, a driving voltage is higher than driving voltages of exemplary embodiments of the present inventive concept (e.g., in a normally black mode or in a normally white mode). Thus, it will be understood that the liquid crystal modulator according to an embodiment of the present inventive concept may have a lower driving voltage than other conventional arts have.

According to an embodiment of the present inventive concept, as described above, lights may be reflected or transmitted to a measurement unit MU through a focusing unit FU depending on whether a voltage is applied to a liquid crystal modulator. Data signals one-to-one corresponding to the lights are generated from the measurement unit MU. When images one-to-one corresponding to the data signals are generated from an image processing unit, an operator may determine whether a display substrate is defective by comparing the images with each other.

As described so far, exemplary embodiments provide a liquid crystal modulator whose driving voltage is low and which is capable of clearly displaying whether pixels are normal or defective. In addition, the exemplary embodiments provide an inspection apparatus including the liquid crystal modulator.

Although the present inventive concept has been described with reference to exemplary embodiments thereof, it will be understood that various modifications in form and details may be made without departing from the spirit and scope of the present inventive concept.

What is claimed is:

1. A liquid crystal modulator for detecting a defect of a substrate, the liquid crystal modulator comprising:
   a reflection layer configured to reflect light;
   an electrode provided on the reflection layer;
   a liquid crystal layer provided between the reflection layer and the electrode and including hybrid aligned nematic liquid crystal molecules whose pre-tilt angle gradually increases from a first alignment layer adjacent to the reflection layer to a second alignment layer adjacent to the electrode, wherein the hybrid aligned nematic liquid crystal molecules near the first alignment layer are substantially horizontal and the hybrid aligned nematic liquid crystal molecules near the second alignment layer are substantially vertical; and
   a polarizer provided on the electrode,
   wherein when the hybrid aligned nematic liquid crystal molecules are arranged along an electric field established by an applied voltage, the hybrid aligned nematic liquid crystal molecules near the first alignment layer remain substantially horizontal.

2. The liquid crystal modulator as set forth in claim 1, wherein a pretilt angle of the vertical alignment layer is between about 89 degrees and about 90 degrees, and a pretilt angle of the horizontal alignment layer is two degrees or less.

3. The liquid crystal modulator as set forth in claim 1, wherein a rubbing axis of the horizontal alignment layer is tilted at an angle of about 45 degrees with respect to a polarizing axis of the polarizer.

4. The liquid crystal modulator as set forth in claim 3, wherein the liquid crystal modulator is driven in a normally black mode.

5. The liquid crystal modulator as set forth in claim 1, further comprising: a quarter wave plate provided between the electrode and the polarizer.

6. The liquid crystal modulator as set forth in claim 5, wherein the quarter wave plate is titled at an angle of about 45 degrees with respect to a polarizing axis of the polarizer.

7. The liquid crystal modulator as set forth in claim 5, wherein the quarter wave plate is substantially parallel or vertical to a rubbing axis of the horizontal alignment layer.

8. The liquid crystal modulator as set forth in claim 5, wherein the liquid crystal modulator is driven in a normally white mode.

9. The liquid crystal modulator as set forth in claim 1, wherein the hybrid aligned nematic liquid crystal molecules have positive dielectric anisotropy.

10. The liquid crystal modulator as set forth in claim 9, wherein the liquid crystal layer delays a phase of one of polarization components of light incident to the liquid crystal layer by a quarter wavelength.

11. An inspection apparatus for detecting a defect of a substrate, the inspection apparatus comprising:
a liquid crystal modulator;
a light emitting unit configured to emit light;
a beam splitter configured to divide the light emitted from the light emitting unit into a plurality of beams and to provide the plurality of beams to the liquid crystal modulator; and
a measurement unit configured to sense a plurality of beams output from the liquid crystal modulator,
wherein the liquid crystal modulator comprises:
a first substrate;
a reflection layer disposed on the first substrate and configured to reflect the plurality of beams provided from the beam splitter;
an electrode disposed on the reflection layer;
a liquid crystal layer provided between the reflection layer and the electrode and including a hybrid aligned nematic liquid crystal;
a second substrate disposed on the electrode;
a polarizer disposed on the second substrate; and
a third substrate disposed on the polarizer.

12. The inspection apparatus as set forth in claim 11, further comprising:
a first alignment layer provided between the liquid crystal layer and the electrode; and
a second alignment layer provided between the reflection layer and the liquid crystal layer,
wherein one of the first and second alignment layers is a horizontal alignment layer and the other is a vertical alignment layer.

13. The inspection apparatus as set forth in claim 12, wherein a rubbing axis of the horizontal alignment layer is tilted at an angle of about 45 degrees with respect to a polarizing axis of the polarizer.

14. The inspection apparatus as set forth in claim 11, wherein the liquid crystal modulator is driven in a normally black mode.

15. The inspection apparatus as set forth in claim 11, further comprising: a quarter wave plate provided between the electrode and the polarizer.

16. The inspection apparatus as set forth in claim 15, wherein the quarter wave plate is tilted at an angle of about 45 degrees with respect to a polarizing axis of the polarizer.

17. The inspection apparatus as set forth in claim 15, wherein the liquid crystal modulator is driven in a normally white mode.

18. The inspection apparatus as set forth in claim 11, wherein the hybrid aligned nematic liquid crystal has positive dielectric anisotropy.

19. The inspection apparatus as set forth in claim 18, wherein the liquid crystal layer delays a phase of one of polarization components of light incident to the liquid crystal layer by a quarter wavelength.

* * * * *